United States Patent
Beselt et al.

(10) Patent No.: US 10,088,305 B2
(45) Date of Patent: Oct. 2, 2018

(54) INDEPENDENTLY DRIVEN, DUAL SIDED SCANNER HEADS

(71) Applicant: Honeywell ASCa Inc., Mississauga (CA)

(72) Inventors: Ronald E. Beselt, Burnaby (CA);
Cristian Andronic, Burnaby (CA);
Gertjan Hofman, Vancouver (CA);
Sudhir Thalore, Burnaby (CA)

(73) Assignee: Honeywell Limited, Ontario (CA)

( * ) Notice: Subject to any disclaimer, the term of this patent is extended or adjusted under 35 U.S.C. 154(b) by 970 days.

(21) Appl. No.: 14/470,744

(22) Filed: Aug. 27, 2014

(65) Prior Publication Data

US 2016/0061601 A1 Mar. 3, 2016

(51) Int. Cl.
*G01N 21/89* (2006.01)
*G01B 7/31* (2006.01)
*G01B 21/24* (2006.01)

(52) U.S. Cl.
CPC ............... *G01B 21/24* (2013.01); *G01B 7/31* (2013.01); *G01N 21/8901* (2013.01); *G01N 21/8903* (2013.01); *G01B 2210/44* (2013.01)

(58) Field of Classification Search
CPC ...... G01B 21/24; G01B 7/31; G01B 2210/44; G01N 21/8901; G01N 21/8903
See application file for complete search history.

(56) References Cited

U.S. PATENT DOCUMENTS

| | | | |
|---|---|---|---|
| 6,281,679 B1 * | 8/2001 | King | G01B 7/107 324/226 |
| 8,564,851 B2 | 10/2013 | Beselt | |
| 2009/0237749 A1 | 9/2009 | Clouse | |
| 2009/0258604 A1 * | 10/2009 | Andronic | G01N 33/346 455/73 |
| 2013/0100503 A1 * | 4/2013 | Beselt | H04N 1/128 358/474 |

OTHER PUBLICATIONS

Notification of Transmittal of the International Search Report and the Written Opinion of the International Searching Authority, or the Declaration dated Oct. 6, 2015 in connection with International Patent Application No. PCT/CA2015/000475.

* cited by examiner

*Primary Examiner* — Paul D Lee
*Assistant Examiner* — Mark Crohn

(57) ABSTRACT

A scanning measurement system includes independently driven, self-aligning, dual-sided heads. The system is configured to perform a method that includes receiving information associated with a discrepancy in a desired cross direction alignment of a first sensor head and a second sensor head that are disposed on opposite sides of a web of material and that are configured to move in a cross direction relative to the web. The method also includes adjusting a velocity of at least one of the sensor heads based on the received information to improve the cross direction alignment of the first sensor head and the second sensor head.

21 Claims, 2 Drawing Sheets

INDEPENDENTLY DRIVEN, DUAL SIDED SCANNER HEADS

TECHNICAL FIELD

This disclosure relates generally to scanning measurement systems. More specifically, this disclosure relates to the alignment of independently driven, dual sided scanner heads.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using one or more scanning heads that move back and forth across the width of the web.

SUMMARY

This disclosure provides a method and system for using independently driven, self-aligning, dual-sided heads in scanning measurement systems.

In a first embodiment, a method includes receiving information associated with a discrepancy in a desired cross direction alignment of a first sensor head and a second sensor head that are disposed on opposite sides of a web of material and that are configured to move in a cross direction relative to the web. The method also includes adjusting a velocity of at least one of the sensor heads based on the received information to improve the cross direction alignment of the first sensor head and the second sensor to head.

In a second embodiment, an apparatus includes a first sensor head that is configured to be disposed on a first side of a web of material. The first sensor head includes at least one controller that is configured to control a motor, where the motor is configured to move the first sensor head in a cross direction relative to the web. The at least one controller is also configured to receive information associated with a discrepancy in a desired cross direction alignment of the first sensor head and a second sensor head that is disposed on a second side of the web opposite the first side. The at least one controller is further configured to adjust a velocity of at least one of the sensor heads based on the received information to improve the cross direction alignment of the first sensor head and the second sensor head.

In a third embodiment, a system includes a first sensor head and a second sensor head. The first sensor head is configured to be disposed on a first side of a web of material and to move in a cross direction relative to the web. The second sensor head is configured to be disposed on a second side of the web opposite the first side and to move in the cross direction. The first sensor head is also configured to receive information associated with a discrepancy in a desired cross direction alignment of the first sensor head and the second sensor head. The first sensor head is further configured to adjust a velocity of at least one of the sensor heads based on the received information to improve the cross direction alignment of the first sensor head and the second sensor head.

In a fourth embodiment, a non-transitory computer readable medium embodies a computer program. The computer program includes computer readable program code for receiving information associated with a discrepancy in a desired cross direction alignment of a first sensor head and a second sensor head that are disposed on opposite sides of a web of material and that are configured to move in a cross direction relative to the web. The computer program also includes computer readable program code for adjusting a velocity of at least one of the sensor heads based on the received information to improve the cross direction alignment of the first sensor head and the second sensor head.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Scanning systems for sheet- or other web-related processes often use translating scanning heads that house sensors and that move back and forth across each side of the web. In many systems, scanning heads are mechanically coupled to a belt system that is mounted to a frame and that is driven by a single motor. In such systems, alignment of the sensors in the scanning direction is determined by the accuracy of the belt tooth structure in the drive system. In some cases, the accuracy of the belt tooth structure is not sufficient at times. This may be due to short-term variations in tooth pitch, belt stretch, reaction force differences between scanning heads, longitudinal vibration modes in the belt structure, or other factors. Embodiments of this disclosure solve the problem of sensor head alignment by allowing both heads to be driven independently, with alignment achieved electronically via one or more position sensors and positional control algorithms.

Figure 1:
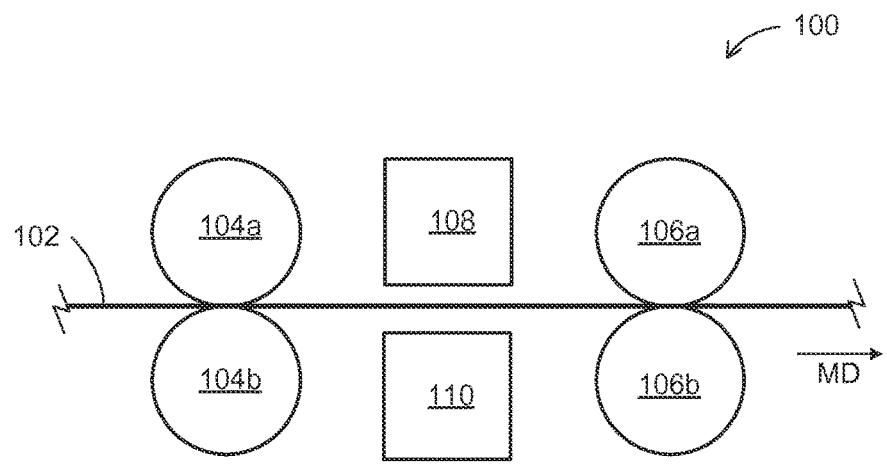
FIG. 1 illustrates a portion of an example web-making or web-processing system in accordance with this disclosure.

FIG. 1 illustrates a portion of an example web-making or web-processing system 100 in accordance with this disclosure. As shown in FIG. 1, the system 100 manufactures or processes a continuous web 102. The web 102 can represent any suitable material or materials manufactured or processed as moving sheets or other webs. Example webs 102 can include paper, multi-layer paperboard, cardboard, plastic, textiles, or metal webs.

In this example, the web 102 is transported through this portion of the system 100 using two pairs of rollers 104a-104b and 106a-106b. For example, the roller pair 104a-104b can pull the web 102 from a previous stage of a web-manufacturing or web-processing system. Also, the roller pair 106a-106b can feed the web 102 into a subsequent stage of the web-manufacturing or web-processing system. The roller pairs 104a-104b and 106a-106b move the web 102 in a direction referred to as the "machine direction" (MD).

Two or more scanning sensor assemblies 108-110 are positioned between the roller pairs 104a-104b and 106a-106b. Each scanning sensor assembly 108-110 includes one or more sensors capable of measuring at least one characteristic of the web 102. For example, the scanning sensor assemblies 108-110 could include sensors for measuring the moisture, caliper, anisotropy, basis weight, color, gloss, sheen, haze, surface features (such as roughness, topography, or orientation distributions of surface features), or any other or additional characteristic(s) of the web 102. In general, a characteristic of the web 102 can vary along the length of the web 102 (in the "machine direction") and/or across the width of the web 102 (in a "cross direction" or "CD"). Each scanning sensor assembly 108-110 includes any suitable structure or structures for measuring or detecting one or more characteristics of a web. Each sensor assembly 108-110 is configured to move back and forth (in the cross direction) across the web 102 in order to measure one or more characteristics across the width of the web 102.

Each scanning sensor assembly 108-110 can communicate wirelessly or over a wired connection with an external device or system, such as a computing device that collects measurement data from the scanning sensor assemblies 108-110. For example, each scanning sensor assembly 108-110 could communicate with an external device or system to synchronize a clock of that sensor assembly 108-110 with the clock of the external device or system.

Unlike some scanner systems in which different assemblies are mechanically coupled to maintain alignment, the scanning sensor assemblies 108-110 are not mechanically coupled and are independently moveable. However, there are many instances in which it is desirable for the scanning sensor assemblies 108-110 to maintain alignment with each other as the sensor assemblies 108-110 move. In accordance with this disclosure, the sensor assembly 108 can be a master sensor assembly, and the sensor assembly 110 can be a follower sensor assembly. The master sensor assembly 108 moves back and forth across all or a portion of the width of the web 102 according to a sensor assembly motion profile. The follower sensor assembly 110 follows the movement of the master sensor assembly 108 in order to maintain alignment with the master sensor assembly 108. For example, the follower sensor assembly 110 can make velocity adjustments in order to improve the alignment as described in greater detail below.

Although FIG. 1 illustrates a portion of one example web-making or web-processing system 100, various changes may be made to FIG. 1. For example, while the scanning sensor assemblies 108-110 are shown here as being used between two pairs of rollers, the scanning sensor assemblies 108-110 could be used in any other or additional location(s) of a web-making or web-processing system. Moreover, FIG. 1 illustrates one operational environment in which alignment techniques for independently driven, dual sided scanner heads can be used. This functionality could be used in any other type of system.

Figure 2:
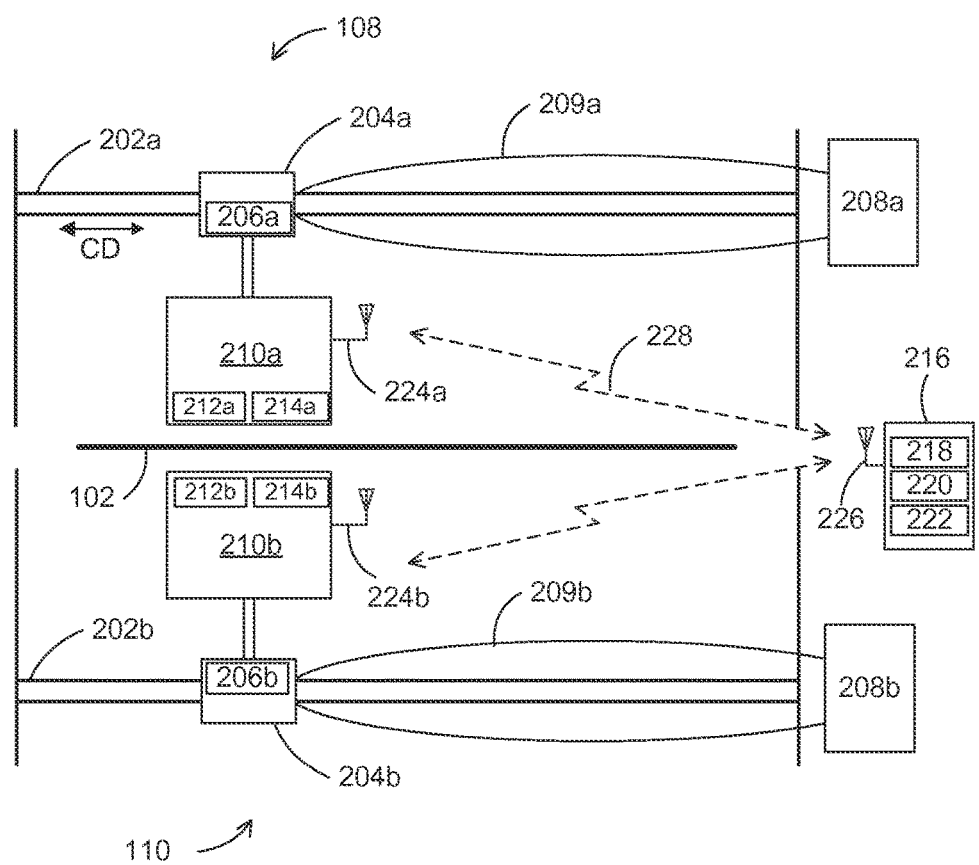
FIG. 2 illustrates example scanning sensor assemblies in the system of FIG. 1 in accordance with this disclosure.

FIG. 2 illustrates example scanning sensor assemblies 108-110 in the system 100 of FIG. 1 in accordance with this disclosure. Much of the structure of the master sensor assembly 108 is the same as or similar to the structure of the follower sensor assembly 110. Where the structure of the follower sensor assembly 110 differs from the structure of the master sensor assembly 108, those differences are highlighted below.

As shown in FIG. 2, each scanning sensor assembly 108-110 includes a respective track 202a-202b on which a respective carriage 204a-204b travels. In the system 100, each track 202a-202b could generally extend in the cross direction across the width of the web 102. Each carriage 204a-204b can traverse back and forth along its track 202a-202b to move one or more sensors back and forth across the web 102. Each track 202a-202b generally includes any suitable structure on which other components of a sensor assembly can move, such as a belt, shaft, or beam formed of metal or another suitable material. Each carriage 204a-204b includes any suitable structure for moving along a track.

Various mechanisms can be used to move the carriages 204a-204b along the tracks 202a-202b or to position the sensor assemblies 108-110 at particular locations along the tracks 202a-202b. For example, each carriage 204a-204b could include a respective motor 206a-206b that moves the carriage 204a-204b along its track 202a-202b. As another example, external motors 208a-208a could move belts 209a-209b that are physically connected to the carriages 204a-204b, where the belts 209a-209b move the carriages 204a-204b along the tracks 202a-202b. Any other suitable mechanism for moving each carriage 204a-204b along its track 202a-202b could be used.

Scanning sensor heads 210a-210b are connected to the carriages 204a-204b. Each sensor head 210a-210b respectively includes at least one web sensor 212a-212b that captures measurements associated with the web 102. Each sensor head 210a-210b includes any suitable structure for carrying one or more sensors. Each web sensor 212a-212b includes any suitable structure for capturing measurements associated with one or more characteristics of a web. A web sensor 212a-212b could represent a contact sensor that takes measurements of a web via contact with the web or a non-contact sensor that takes measurements of a web without contacting the web.

Each sensor head 210a-210b also respectively includes at least one position sensor element 214a-214b for capturing relative or absolute "cross direction" positional information of that sensor head 210a-210b for use in aligning the sensor assemblies 108-110. Each position sensor element 214a-214b includes any suitable structure for capturing positional information of a corresponding sensor head. In some embodiments, the position sensor element 214a associated with the master sensor assembly 108 includes a magnet, and the position sensor element 214b associated with the follower sensor assembly 110 includes a magnetic sensor. In these embodiments, the magnetic sensor (position sensor element 214b) can sense the magnet (position sensor element 214a) through the web 102 and determine a difference in cross direction position of the follower sensor assembly 110 relative to the master sensor assembly 108. In other embodiments, each position sensor element 214a-214b includes an independent position sensor configured to determine a cross direction position relative to the web 102 or another calibrated reference point, such as a linear scale. Such position sensors may be useful when a magnetic sensor cannot be used. In still other embodiments, each position sensor element 214a-214b includes a combination of two or more of the magnet, the magnetic sensor, and the independent position sensor.

Power can be provided to each sensor head 210a-210b in any suitable manner. For example, each sensor head 210a-210b could be coupled to one or more cables that provide power to that sensor head. As another example, each carriage 204a-204b could ride on one or more cables or rails used to supply power to the associated sensor head 210a-210b. Each sensor head 210a-210b could further include an internal power supply, such as a battery or an inductive coil used to receive power wirelessly. Each sensor head 210a-210b could be powered in any other or additional manner.

In this example, each sensor head 210a-210b can send sensor measurement data to an external controller 216. The controller 216 could use the measurement data in any suitable manner. For example, the controller 216 could use the measurement data to generate CD profiles of the web 102. The controller 216 could then use the CD profiles to determine how to adjust operation of the system 100. The controller 216 could also use the CD profiles or the measurement data to support monitoring applications, process historian applications, or other process control-related applications.

The controller 216 includes any suitable structure(s) for receiving sensor measurement data, such as one or more computing devices. In particular embodiments, the controller 216 includes one or more processing devices 218, such as one or more microprocessors, microcontrollers, digital signal processors, field programmable gate arrays, or application specific integrated circuits. The controller 216 also includes one or more memories 220, such as one or more volatile and/or non-volatile storage devices, configured to store instructions and data used, generated, or collected by the processing device(s) 218. In addition, the controller 216 includes one or more interfaces 222 for communicating with external devices or systems, such as one or more wired interfaces (like an Ethernet interface) or one or more wireless interfaces (like a radio frequency transceiver). The controller 216 could represent all or part of a centralized control system or part of a distributed control system. In particular embodiments, the controller 216 includes a measurement subsystem (MSS), which interacts with the sensor assemblies 108a-108b to obtain and process measurements of the web 102. The processed measurements can then be provided to other components of the controller 216.

Each sensor head 210a-210b and the controller 216 can communicate wirelessly or via a wired connection. In the embodiment shown in FIG. 2, each sensor head 210a-210b is configured for wireless communication and respectively includes at least one antenna 224a-224b, and the controller 216 includes at least one antenna 226. The antennas 224-226 support the exchange of wireless signals 228 between the sensor heads 210a-210b and the controller 216. For example, the controller 216 could transmit commands instructing the sensor heads 210a-210b to capture measurements of the web 102, and the sensor heads 210a-210b can transmit web measurements, positional information, and associated alignment data to the controller 216. The sensor heads 210a-210b could also transmit other data to the controller 216, such as diagnostic data. Each antenna 224a, 224b, 226 includes any suitable structure for transmitting wireless signals, such as radio frequency signals.

As noted above, the scanning sensor assemblies 108-110 operate in order to maintain alignment between the sensor heads 210a-210b. That is, the carriage 204a of the master sensor assembly 108 moves back and forth along the track 202a according to a motion profile (thereby moving the sensor head 210a). At the same time, the carriage 204b of the follower sensor assembly 110 follows the movement of the master sensor assembly 108 so that the sensor heads 210a-210b maintain substantially the same cross direction location or a substantially fixed offset that does not change with movement. Note that the term "alignment" here refers to a desired relationship between sensor heads, including situations where the sensor heads have substantially the same cross direction position and situations where the sensor heads have a desired amount of offset in their cross direction positions.

Various techniques may be used by the follower sensor assembly 110 to improve or maintain the desired alignment with the master sensor assembly 108. In one technique, the follower sensor assembly 110 uses a position feedback control loop for feeding back information in order to operate or control one or both of the motors 206a-206b. In the position feedback control loop, the follower sensor assembly 110 receives movement direction, relative position, velocity information, or a combination of these from the position sensor element 214a, the position sensor element 214b, or both. In some embodiments, this may include the follower sensor assembly 110 receiving relative position information from a magnetic sensor based on its sensing of a magnet. The feedback information can be measured with respect to the master sensor assembly 108, the follower sensor assembly 110, or both. The follower sensor assembly 110 then utilizes the feedback information to adjust its velocity profile to improve or maintain relative alignment with the master sensor assembly 108.

In order to maintain accuracy in the alignment, measurements can be taken many times per second, and the velocity of one or both of the motors 206a-206b is adjusted if a discrepancy is noted to allow the follower sensor assembly 110 to re-align with the master sensor assembly 108. In some embodiments, the master sensor assembly 108 moves according to a preferred motion profile and it may be assumed that the master sensor assembly 108 is always at a correct position, adjustments for alignment are only made to the follower sensor assembly 110.

In another technique, the follower sensor assembly 110 uses a position feed forward control loop. Due to the repetitive nature of many scanning systems, the movements of the master sensor assembly 108 and the follower sensor assembly 110 can be examined over time, and a movement profile for each sensor assembly 108-110 can be determined. Differences between the movement profiles due to unintended misalignments can be recorded as error signals. In many cases, an error signal is similar from scan to scan in the same direction. This signal can be time averaged for a given direction and combined with the general motion profile to provide a feed forward error correction. By determining a current position of one or both of the sensor assemblies 108-110 and identifying a historically determined feed forward error correction corresponding to that position, the follower sensor assembly 110 can estimate the expected misalignment for that position of the sensor heads 210a-210b and adjust the velocity profile accordingly. In some embodiments, this feed forward control loop technique can be used with the feedback control loop technique to further maintain or improve alignment.

In still another technique, the follower sensor assembly 110 uses absolute cross direction positions of each sensor assembly 108-110 to determine relative alignment. For example, each position sensor element 214a-214b can include a position sensor or encoder configured to determine a cross direction position of the respective assembly relative to the web 102 or another calibrated reference point, such as a linear scale along the track 202a-202b. Each position sensor 214a-214b can also include a clock. When the position sensors or encoders are time-synchronized (the clocks of the position sensors or encoders read the same time), the position sensors or encoders can be read to determine the cross direction position of the sensor assemblies 108-110 at a particular moment, and velocity adjustments can be made if the cross direction positions are not the same. This technique allows alignment adjustments to be made without the use of a magnetic sensor. This can be important where the use of a magnetic sensor is not permitted (such as when the web 102 is a metallic foil that interferes with magnetic fields) or where a magnet would be separated too far from a magnetic sensor.

In some embodiments, one or both position sensor elements 214a-214b can include an accelerometer sensor. In such embodiments, acceleration readings can be used with position or velocity readings to further smooth out motion of one or both sensor assemblies 108-110 by allowing inertial feedback to be combined with drive signals to reduce longitudinal vibrations. This may also help to prevent the follower sensor assembly 110 from developing destructive error profiles.

As noted above, "alignment" of the sensor heads 210a-210b does not require that the sensor heads be located at the same cross direction position. For example, the sensor heads 210a-210b could be separated by a predetermined fixed offset. As a particular example, it may be desirable to have the sensor heads maintain a 3 cm offset (or any other suitable amount) in the cross direction, regardless of absolute position or velocity, due to a particular web processing step. Because the sensor assemblies 108-110 are independently controlled and driven, it is possible to switch from maintaining a zero offset to maintaining another fixed offset without having to change or adjust hardware. In addition, because the sensor assemblies 108-110 are independently controlled, the sensor assemblies 108-110 can be intentionally split (deliberately misaligned) in order to perform service tasks (such as head cleaning) or for any other suitable reason.

Although FIG. 2 illustrates one example of the scanning sensor assemblies 108-110 in the system 100 of FIG. 1, various changes may be made to FIG. 2. For example, various components in each scanning sensor assembly 108-110 could be combined, further subdivided, or omitted and additional components could be added according to particular needs. In addition, the form of each assembly with a carriage 204a-204b connected to a separate sensor head 210a-210b is for illustration only. Each sensor head 210a-210b could incorporate or be used with a carriage in any suitable manner. Also, while FIG. 2 has described an example with a master sensor assembly 108 and a follower sensor assembly 110, in other embodiments, the sensor assembly 110 may be the master and the sensor assembly 108 may be the follower. In still other embodiments, both sensor assemblies 108-110 may be followers that move according to control instructions from a controller, such as the controller 216.

Figure 3:
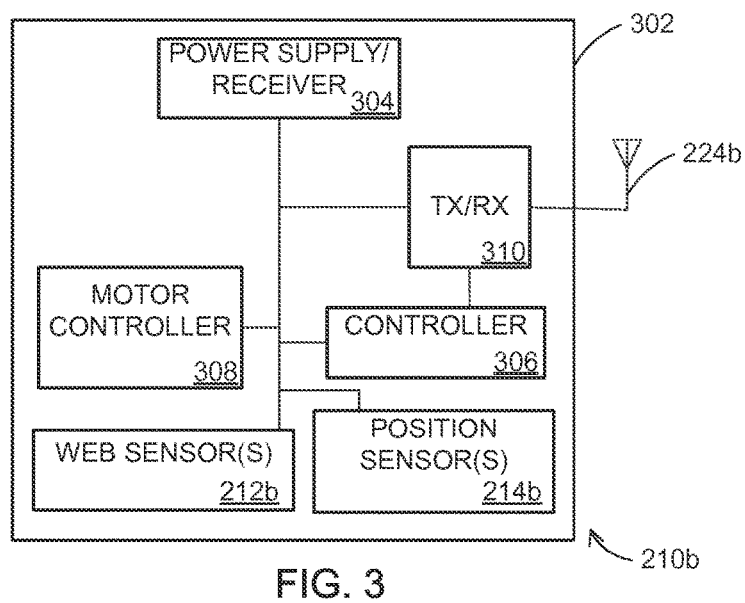
FIG. 3 illustrates an example scanning sensor head in the scanning sensor assembly of FIG. 1 in accordance with this disclosure.

FIG. 3 illustrates an example scanning sensor head 210b in the scanning sensor assembly 110 of FIG. 1 in accordance with this disclosure. It will be understood that the scanning sensor head 210a could be configured the same as or similar to the scanning sensor head 210b.

As shown in FIG. 3, the sensor head 210b includes a moveable chassis 302, which represents a housing or other structure configured to encase, contain, or otherwise support other components of the sensor head 210b. The chassis 302 can be formed from any suitable material(s) (such as metal) and in any suitable manner.

As described above, the sensor head 210b includes at least one web sensor 212b and at least one position sensor element 214b. The sensor head 210b also includes a power supply/receiver 304, which provides operating power to the sensor head 210b. For example, the power supply/receiver 304 could receive AC or DC power from an external source, and the power supply/receiver 304 could convert the incoming power into a form suitable for use in the sensor head 210b. The power supply/receiver 304 includes any suitable structure(s) for providing operating power to the sensor head 210b, such as an AC/DC or DC/DC power converter. The power supply/receiver 304 may also include a battery, capacitor, or other power storage device.

A controller 306 controls the overall operation of the sensor head 210b. For example, the controller 306 could receive measurements associated with one or more characteristics of the web 102 from the web sensor 212. The controller 306 could also receive positional measurements associated with the position or velocity of the sensor head 210b from the position sensor element 214b. The positional measurements could correlate the position of the sensor head 210b with respect to another sensor head or with respect to the web 102 or a reference point. The controller 306 could further control the transmission of this data to the controller 216 or other destination(s). The controller 306 includes any suitable processing or control device(s), such as one or more microprocessors, microcontrollers, digital signal processors, field programmable gate arrays, or application specific integrated circuits. Note that the controller 306 could also be implemented as multiple devices.

A motor controller 308 can be used to control the operation of one or more motors, such as one or more of the motors 206a-206b, 208a-208b. For example, the motor controller 308 could generate and output pulse width modulation (PWM) or other control signals for adjusting the direction and speed of the motor 206b. The direction and speed could be controlled based on input from the controller 306. The motor controller 308 includes any suitable structure for controlling operation of a motor.

A wireless transceiver 310 is coupled to the antenna(s) 224b. The wireless transceiver 310 facilitates the wireless transmission and reception of data, such as by transmitting web measurements, positional measurements, and related data to the controller 216 and receiving commands from the controller 216. The wireless transceiver 310 includes any suitable structure for generating signals for wireless transmission and/or for processing signals received wirelessly. In particular embodiments, the wireless transceiver 310 represents a radio frequency (RF) transceiver. Note that the transceiver 310 could be implemented using a transmitter and a separate receiver.

In some embodiments, the sensor head 210b operates as follows to maintain or improve alignment between the scanning sensor assemblies 108-110. One or more position sensors 214b measure or determine movement direction, relative position, velocity information, or a combination of these. The measurements are provided to the controller 306, which uses one or more of the techniques described above to determine an alignment correction for one or both sensor assemblies 108-110. For example, depending on the embodiment, the controller 306 may implement a position feedback control loop, a position feed forward control loop, an absolute position, or a combination of two or more of these to determine the alignment correction. Based on the alignment correction, the controller 306 sends signals to the motor controller 308, which in turn adjusts the velocity of the motor 206*b* or other motor(s) or the velocity profile of the respective sensor assembly 108-110.

Although FIG. 3 illustrates one example of a scanning sensor head 210*b* in the scanning sensor assembly 110 of FIG. 1, various changes may be made to FIG. 3. For example, various components in FIG. 3 could be combined, further subdivided, or omitted and additional components could be added according to particular needs. As a particular example, a single controller or more than two controllers could be used to implement the functions of the controllers 306-308. Additionally or alternatively, one or both controllers 306-308 could be located external to the scanning sensor head 210*b*, such as at the external controller 216 or at any other suitable location.

Figure 4:
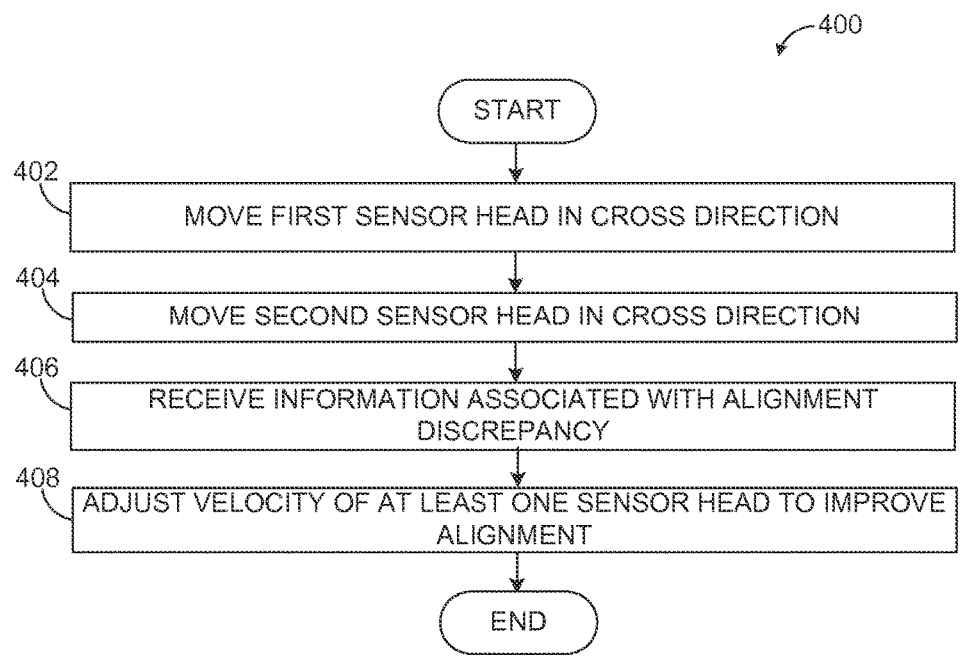
FIG. 4 illustrates an example method for alignment of independently driven scanning sensor heads in accordance with this disclosure.

FIG. 4 illustrates an example method 400 for alignment of independently driven scanning sensor heads in accordance with this disclosure. For ease of explanation, the method 400 is described with respect to the scanning sensor assemblies 108-110 of FIG. 2 operating in the system 100 of FIG. 1. Of course, the method 400 could be performed by any other suitable device(s) and in any other suitable system(s).

As shown in FIG. 4, a first sensor head moves in a cross direction relative to a web of material at step 402. The first sensor head is disposed on a first side of the web. The first sensor head could be part of a master sensor assembly. For example, this could include the sensor head 210*a* of the master sensor assembly 108 moving in a cross direction relative to the web 102.

A second sensor head moves in the cross direction at step 404. The second sensor head is disposed on a second side of the web opposite the first side. The second sensor head could be part of a follower sensor assembly. For example, this could include the sensor head 210*b* of the follower sensor assembly 110 moving in a cross direction relative to the web 102.

Information associated with a discrepancy in a desired cross direction alignment of the first sensor head and the second sensor head is received at step 406. The received information could include data from a magnetic sensor coupled to one of the sensor heads, which senses a magnet coupled to the other sensor head. The received information could also include absolute position information from a first position sensor coupled to the first sensor head and absolute position information from a second position sensor coupled to the second sensor head. Any other suitable position-related information could be used to identify the discrepancy in the desired cross direction alignment of the sensor heads.

Based on the received information, the velocity of at least one of the sensor heads is adjusted at step 408 to improve the cross direction alignment of the first sensor head and the second sensor head. In some embodiments, this may include using the received information in a position feedback control loop to determine an adjusted velocity or in a position feed forward control loop to determine an adjusted velocity, where the position feed forward control loop includes an estimated misalignment based on a historically determined error correction.

In some embodiments, the sensor heads could be deliberately misaligned before performing a service operation on one of the heads or the overall system. Also, in some embodiments, the desired cross direction alignment could be changed from a zero offset to a non-zero offset based on a type of web manufacturing or processing that is occurring or is to occur.

Although FIG. 4 illustrates one example of a method 400 for alignment of independently driven scanning sensor heads, various changes may be made to FIG. 4. For example, while shown as a series of steps in each figure, various steps in FIG. 4 could overlap, occur in parallel, occur in a different order, or occur any number of times. Also, certain steps could be separately performed by multiple sensor heads 210*a*-210*b* scanning the same web 102, such as on different sides of the web 102. In this way, different components can receive and correlate sensor measurements from multiple sensor heads 210*a*-210*b* on opposite sides of the web 102.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
receiving information associated with a discrepancy in a cross direction alignment of a first sensor head and a second sensor head that are disposed on opposite sides of a web of material, the first sensor head configured to move along a first track in a cross direction relative to the web, the second sensor head configured to move along a second track in the cross direction; and
controlling a first motor associated with the first sensor head to adjust a velocity of the first sensor head relative to a velocity of the second sensor head based on the received information to improve the cross direction alignment of the first sensor head and the second sensor head,
wherein the first motor is different from a second motor associated with the second sensor head, and
wherein the received information comprises first absolute cross direction position information from a first position sensor coupled to the first sensor head and second absolute cross direction position information from a second position sensor coupled to the second sensor head, wherein the first absolute cross direction position information is determined relative to a first calibrated scale along the first track and the second absolute cross direction position information is determined relative to a second calibrated scale along the second track.

2. The method of claim 1, wherein adjusting the velocity of the first sensor head comprises using the received information in a position feedback control loop to determine an adjusted velocity of the first sensor head.

3. The method of claim 1, wherein:
adjusting the velocity of the first sensor head comprises using the received information in a position feed forward control loop to determine an adjusted velocity of the first sensor head; and
the position feed forward control loop uses an estimated misalignment based on a historically determined error correction.

4. The method of claim 1, wherein the received information further comprises a difference in cross direction position or velocity between the first sensor head and the second sensor head.

5. The method of claim 1, wherein the cross direction alignment of the first sensor head and the second sensor head comprises a desired offset in cross direction positions of the sensor heads.

6. The method of claim 5, further comprising:
changing the desired offset between a zero offset value and a non-zero offset value.

7. An apparatus comprising:
a first sensor head configured to be disposed on a first side of a web of material, the first sensor head comprising at least one controller configured to:
control a first motor configured to move the first sensor head along a first track in a cross direction relative to the web;
receive information associated with a discrepancy in a cross direction alignment of the first sensor head and a second sensor head disposed on a second side of the web opposite the first side, the second sensor head configured to move along a second track in the cross direction; and
control the first motor to adjust a velocity of the first sensor head relative to a velocity of the second sensor head based on the received information to improve the cross direction alignment of the first sensor head and the second sensor head,
wherein the first motor is different from a second motor configured to move the second sensor head, and
wherein the received information comprises first absolute cross direction position information from a first position sensor coupled to the first sensor head and second absolute cross direction position information from a second position sensor coupled to the second sensor head, wherein the first absolute cross direction position information is determined relative to a first calibrated scale along the first track and the second absolute cross direction position information is determined relative to a second calibrated scale along the second track.

8. The apparatus of claim 7, wherein the at least one controller is configured to use the received information in a position feedback control loop to determine an adjusted velocity of the first sensor head.

9. The apparatus of claim 7, wherein:
the at least one controller is configured to use the received information in a position feed forward control loop to determine an adjusted velocity of the first sensor head; and
the position feed forward control loop uses an estimated misalignment based on a historically determined error correction.

10. The apparatus of claim 7, wherein the received information further comprises a difference in cross direction position or velocity between the first sensor head and the second sensor head.

11. The apparatus of claim 7, wherein the cross direction alignment of the first sensor head and the second sensor head comprises a desired offset in cross direction positions of the sensor heads.

12. The apparatus of claim 11, wherein the at least one controller is further configured to change the desired offset between a zero offset value and a non-zero offset value.

13. A system comprising:
a first sensor head and a second sensor head, the first sensor head configured to be disposed on a first side of a web of material and to move along a first track in a cross direction relative to the web, the second sensor head configured to be disposed on a second side of the web opposite the first side and to move along a second track in the cross direction;
a first motor configured to move the first sensor head; and
a second motor configured to move the second sensor head,
wherein the first sensor head is further configured to:
receive information associated with a discrepancy in a cross direction alignment of the first sensor head and the second sensor head; and
control the first motor to adjust a velocity of the first sensor head relative to a velocity of the second sensor head based on the received information to improve the cross direction alignment of the first sensor head and the second sensor head,
wherein the received information comprises first absolute cross direction position information from a first position sensor coupled to the first sensor head and second absolute cross direction position information from a second position sensor coupled to the second sensor head, wherein the first absolute cross direction position information is determined relative to a first calibrated scale along the first track and the second absolute cross direction position information is determined relative to a second calibrated scale along the second track.

14. The system of claim 13, wherein the first sensor head is configured to use the received information in a position feedback control loop to determine an adjusted velocity of the first sensor head.

15. The system of claim 13, wherein:
the first sensor head is configured to use the received information in a position feed forward control loop to determine an adjusted velocity of the first sensor head; and
the position feed forward control loop uses an estimated misalignment based on a historically determined error correction.

16. The system of claim 13, wherein the received information further comprises a difference in cross direction position or velocity between the first sensor head and the second sensor head.

17. The system of claim 13, wherein the cross direction alignment of the first sensor head and the second sensor head comprises a desired offset in cross direction positions of the sensor heads.

18. A non-transitory computer readable medium embodying a computer program, the computer program comprising computer readable program code for:
receiving information associated with a discrepancy in a cross direction alignment of a first sensor head and a second sensor head that are disposed on opposite sides of a web of material the first sensor head configured to move along a first track in a cross direction relative to the web, the second sensor head configured to move along a second track in the cross direction; and
controlling a first motor associated with the first sensor head to adjust a velocity of the first sensor head relative to a velocity of the second sensor head based on the received information to improve the cross direction alignment of the first sensor head and the second sensor head,
wherein the first motor is different from a second motor associated with the second sensor head, and
wherein the received information comprises first absolute cross direction position information from a first position sensor coupled to the first sensor head and second absolute cross direction position information from a second position sensor coupled to the second sensor head, wherein the first absolute cross direction position information is determined relative to a first calibrated scale along the first track and the second absolute cross direction position information is determined relative to a second calibrated scale along the second track.

19. The non-transitory computer readable medium of claim 18, wherein adjusting the velocity of the first sensor head comprises using the received information in a position feedback control loop to determine an adjusted velocity of the first sensor head.

20. The non-transitory computer readable medium of claim 18, wherein:
adjusting the velocity of the first sensor head comprises using the received information in a position feed forward control loop to determine an adjusted velocity of the first sensor head; and
the position feed forward control loop uses an estimated misalignment based on a historically determined error correction.

21. The non-transitory computer readable medium of claim 18, wherein the received information further comprises a difference in cross direction position or velocity between the first sensor head and the second sensor head.

* * * * *